(12) United States Patent
Dangoisse

(10) Patent No.: US 9,408,999 B2
(45) Date of Patent: Aug. 9, 2016

(54) VASCULAR NEEDLE SYSTEM

(76) Inventor: Vincent Dangoisse, Aiseau-Presles (BE)

(*) Notice: Subject to any disclaimer, the term of this patent is extended or adjusted under 35 U.S.C. 154(b) by 0 days.

(21) Appl. No.: 14/002,294

(22) PCT Filed: Feb. 29, 2012

(86) PCT No.: PCT/EP2012/053457
§ 371 (c)(1),
(2), (4) Date: Nov. 4, 2013

(87) PCT Pub. No.: WO2012/117028
PCT Pub. Date: Sep. 7, 2012

(65) Prior Publication Data
US 2014/0052066 A1   Feb. 20, 2014

Related U.S. Application Data

(60) Provisional application No. 61/448,084, filed on Mar. 1, 2011.

(30) Foreign Application Priority Data

Mar. 2, 2011 (EP) .................. 11156533

(51) Int. Cl.
*A61M 25/06* (2006.01)
*A61B 5/15* (2006.01)
(Continued)

(52) U.S. Cl.
CPC .......... *A61M 25/0693* (2013.01); *A61B 5/1411* (2013.01); *A61B 5/15003* (2013.01); *A61B 5/1535* (2013.01); *A61B 5/150389* (2013.01); *A61B 5/150488* (2013.01); *A61B 5/150496* (2013.01); *A61B 5/150511* (2013.01); *A61B 5/150519* (2013.01); *A61B 5/150732* (2013.01); *A61M 5/3291* (2013.01);

(Continued)

(58) Field of Classification Search
CPC ............... A61M 25/0606; A61M 25/0693; A61M 5/3291; A61M 5/1535; A61M 5/1545; A61M 2005/3201
USPC ............. 604/168.01, 164.01, 164.07, 164.11, 604/166.01
See application file for complete search history.

(56) References Cited

U.S. PATENT DOCUMENTS 5,704,914 A   1/1998   Stocking et al.
2003/0153874 A1   8/2003   Tal
(Continued)

FOREIGN PATENT DOCUMENTS

WO   2007070584   6/2007

OTHER PUBLICATIONS

European Patent Office International Search Report dated Sep. 25, 2012, International Application No. PCT/EP2012/053457 (4 pages).

*Primary Examiner* — Nathan R Price
*Assistant Examiner* — Anh Bui
(74) *Attorney, Agent, or Firm* — Koppel, Patrick, Heybl & Philpott

(57) ABSTRACT

Vascular needle system for visualization of blood has a vascular needle and a tube having a beveled distal end and a proximal end and between the ends a tubular wall having an external surface and an axial cavity for the passage of a fluid between said ends, the needle being provided with at least one lateral aperture and a proximal base-body, the vascular needle system also having a plastic transparent tubular cannula having an internal surface and overlying at least partially the needle.

13 Claims, 4 Drawing Sheets

(51) Int. Cl.
*A61B 5/153* (2006.01)
*A61M 5/32* (2006.01)
*A61B 5/154* (2006.01)

(52) U.S. Cl.
CPC ......... *A61M 25/0606* (2013.01); *A61B 5/1545* (2013.01); *A61M 2005/3201* (2013.01)

(56) References Cited

U.S. PATENT DOCUMENTS

2008/0262430 A1 10/2008 Anderson et al.
2008/0262431 A1* 10/2008 Anderson et al. .......... 604/164.1

* cited by examiner

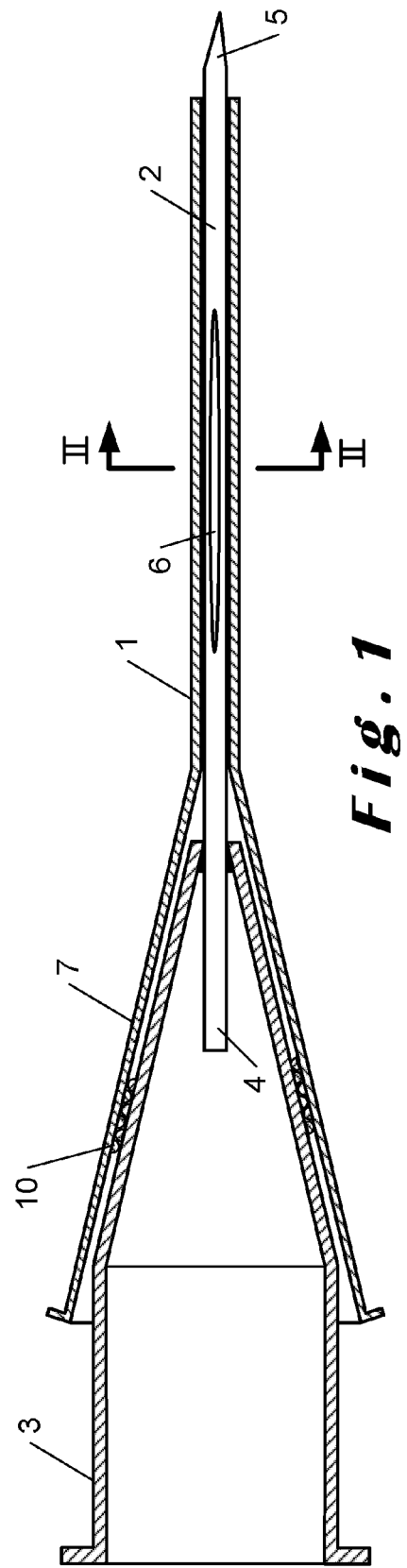

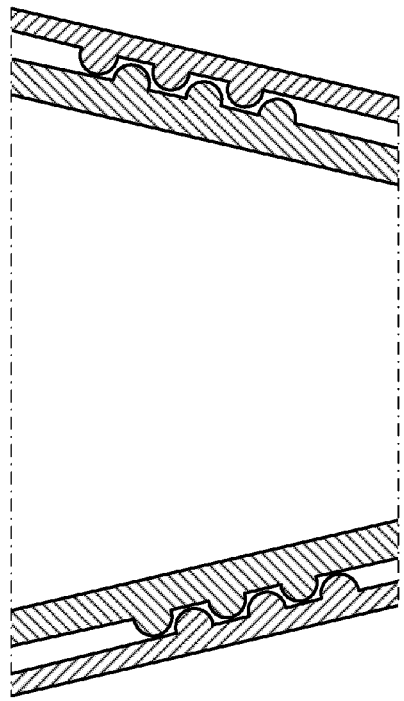
Fig. 1a
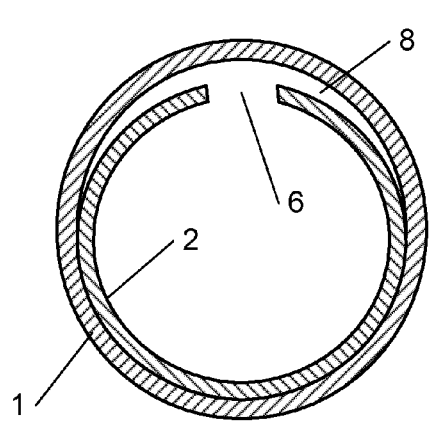 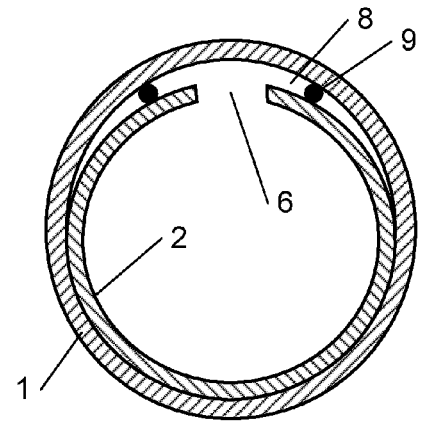
Fig. 2      Fig. 2a

VASCULAR NEEDLE SYSTEM

FIELD OF THE INVENTION

The present invention relates to a vascular needle system for visualisation of blood comprising a vascular needle comprising a tube having a bevelled distal end and a proximal end and between said ends a tubular wall having an external surface and an axial cavity for the passage of a fluid between said ends, said needle being provided with at least one lateral aperture, a proximal base-body fastened to the proximal end of the tube, said vascular needle system also comprising a transparent tubular cannula having an internal surface and overlying at least partially said needle.

BACKGROUND OF THE INVENTION

Numerous interventions in the medical area, for therapeutic as for diagnostic purpose, require access to the vascular system (veins or arteries). Access is obtained by direct puncture of vessels through the skin with a needle. Needles are usually made of a hollow tube, which is usually metallic and is beveled at one end (the distal end) and embedded in a plastic (and transparent) or metallic hub- or base-body on the other end (the proximal end).

Puncture is most of the times "blind", except for venipuncture at the forearm/wrist level where veins can often be seen if compression is applied to the arm, above the puncture site. Otherwise vessel puncture is guided by palpation of the pulse, for artery, or by the supposed anatomic location for deep veins (e.g. jugular or femoral veins).

The success of vessel puncture relies in the outward flow of blood through the needle. For intra-venous drug or fluid injection, puncture of the vein is in general accomplished with a system made of a plastic tube ("cannula") sliding over a hollow metallic needle: as soon as blood flows outside the hub- or base-body of the metallic needle, the plastic cannula is inserted more deeply in the vein, over the metallic needle which is removed thereafter. The cannula can now be attached to a perfusion system with a standardized connection, for example a "luer-lock" connection.

This kind of system (metallic needle+plastic cannula) can also be used for artery access, but most of the time, another technique is in use: the bare metal needle punctures the vessel, then the next step consists of pushing gently a tiny soft and floppy wire (preferably metallic with or without a hydrophilic coating) within the artery lumen through the hollow cavity of the needle. Guided by the wire laying in the lumen of the artery, the needle may be afterwards withdrawn and a material device comprising a plastic tube ("introducer" or "sheath") overlaying a longer and distally tapered plastic tube ("dilator") is inserted over the wire in the lumen of the vessel: it is the <<Seldinger>> technique.

In all cases, the blood outward flow at the base-body of the needle is the sign of a successful vascular access. However the observation of the blood in the base-body can be delayed, particularly for small vessels and in case of low vascular pressure (as in the veins, in general) or when working with long needles or small diameter needles. Thus, despite a correct access into the vessel lumen, the operator will continue to search the vessel and move inadvertently the needle . . . . This can result in an unsuccessful or painful or traumatic and/or hemorrhagic vascular access. Obtaining a quicker visualization of the blood outward flow in order to facilitate and make safer the operator's task of blood vessel puncturing therefore is desirable. Techniques to allow observation of blood after the puncturing a blood vessel include the <<basic>> technique of using transparent hub at the base of the needle, but also more elaborated ways as making aperture(s) or window(s) through the needle and to overlying tubes, making channels between different overlying tubes and using transparent material.

For example, the documents US 2008/0262431 and US 2008/0262430 describe a system firstly comprising a needle and secondly a dilator, disposed on and slideable along the body of the needle and thirdly, a medical article (a sheath), at least partially made of clear, translucent material, which is disposed on and slideable along the dilator. The needle itself has at least one aperture/fenestration (of any shape/length), as the dilator itself: through these apertures, the blood entering the lumen of the needle will flow into space/channel(s) created between the dilator and the sheath. Several ways of creating space between the dilator and the sheath are described, as by modifying the overall circumferential shape (rounded or oval, e.g.) either of the outer surface of the dilator or the inner surface of the sheath, or as by creating ridges along the outer surface of the dilator or the inner surface of the sheath.

The document US 2003/0153874 describes a vascular access system which comprises firstly a needle with at least one opening proximally positioned, secondly a transparent dilator having an annular recess therebetween, the dilator having a passage-way so that the dilator is coaxially positioned around the needle. Thirdly and optionally, a sheath, also transparent fits coaxially over the dilator and there is opening through the dilator allowing the blood to flow from the dilator to an annular space between the dilator and the sheath. The blood may flow through an optional side port in connection to the dilator. The system also uses a guidewire forwarded within the lumen's vessel through the lumen's needle. The dilator and the sheath are preferably clear, semi-opaque or translucent so that the operator can see the blood when blood flows into needle and then through opening into an annular space between needle and dilator, or into or through spaces in the dilator, or through an opening into an annular space between dilator and sheath.

The document WO 2007/070584 describes a needle with a transparent or translucent portion. This document describes a needle in which the inner member is made of metal or other opaque material and the outer member has a transparent or translucent portion. The inner member has one or more openings that permit the uses to visualize what is in the inner member, i.e., blood or medicine. These two tubes may be joined together to form one needle, although in various embodiments, they can act as either single or double lumen needles. The needle according to this document is employed to gain access to blood vessels for introduction of a medical device, e.g., a cardiac catheter for angioplasty.

The document U.S. Pat. No. 5,704,914 describes a system allowing visualization of the blood through a transparent/clear hub since this system comprises rigid clear plastic so that blood can be observed therein upon successful penetration of the lumen of a blood vessel by the needle tip. The system uses also a guidewire to be forwarded through the lumen's needle.

Unfortunately, such devices do not provide a permanently correct detection of blood directly viewable between said needle and said plastic sheath (cannula) since said external surface of the needle may stick against said internal surface of said sheath (cannula) and so prevent the passage of blood. Moreover, according to the documents US2008/0262431, US2008/0262430 and US2003/0153874, said apertures allowing visualization of blood are located both in the dilator and at the level of said needle, requiring some re-direction of the blood flow thereby delaying the visualization and increasing the final size of the apparatus, making the apparatus not suitable for access of small calibre vessels.

SUMMARY OF THE INVENTION

The object of the present invention is consequently to obviate these problems and to obtain a quick visualization of the blood outward flow at the level of the needle in order to facilitate and make safer the operator's task, ensuring, at the same time, a correct detection and direct visualization of blood between the external surface of the needle and the internal surface of said sheath (cannula).

The present invention provides therefore a vascular needle system as indicated in the preamble of the description characterized in that said vascular needle system further comprises a detection cavity for said fluid provided for maintaining said at least one lateral aperture at distance from said internal surface of said cannula, so creating a space between said at least one lateral aperture and said internal surface of said cannula for collecting and detecting said fluid.

Such a vascular needle system allows a quick visualization of the blood outward flow at the level of the needle and ensures a correct detection of blood between the external surface of the needle and the internal surface of said sheath (cannula) because said detection cavity is provided for maintaining a distance between said at least one lateral aperture and said internal surface of said cannula. The presence of said detection cavity creates a small space between said external surface of said needle and said internal surface of the cannula, said space being immediately contaminated by blood coming through the needle's aperture(s) as soon as the needle tip enters a blood vessel. Furthermore, in such a vascular needle system, fluid (blood) has not to flow through channels or complicated circuits.

The above mentioned detection cavity is preferably provided larger than said at least one lateral aperture or smaller, at least partially superimposed to said at least one lateral aperture in fluid connection with said at least one lateral aperture.

According to an embodiment, said detection cavity between said at least one lateral aperture and said internal surface of said cannula is formed by a deformation outward of said cannula with respect to the luminar body of said cannula, for example by suction, traction, heating, molding, to form, for example, an oval or a semi-oval shape. According to this embodiment, said cannula has, in the cross-section, circular shapes at a distal end and at a proximal end of said needle but an oval or semi-oval shape at the level of the aperture of said needle. This means that the cannula only presents an oval or semi-oval shape at the level of the aperture while the cannula sticks to the needle either side of the aperture.

According to another embodiment, said detection cavity between said at least one lateral aperture and said internal surface of said cannula is formed by a deformation of said needle at the level of proximal and/or distal ends of the aperture, for example by forming an oval or a semi-oval section.

According to an alternative embodiment, said detection cavity between said at least one lateral aperture and said internal surface of said cannula is formed by withdrawing a part of the material, either of the material forming the internal wall of the cannula, either of the material forming the external wall of the needle.

According to an alternative embodiment, said detection cavity between said at least one lateral aperture and said internal surface of said cannula is obtained via at least one reinforcing shoulder located between said external surface of said tubular wall of said needle and said internal surface of said cannula, at least one lateral aperture being maintained at distance from said internal surface of said cannula by said at least one reinforcing shoulder.

The above mentioned at least one reinforcing shoulder is connected to said internal surface of said cannula, preferably is a part of said internal surface of said cannula.

In another embodiment, the above mentioned at least one reinforcing shoulder is connected to said external surface of said tubular wall of said needle or is a part of said external surface of said tubular wall of said needle.

Preferably, the above mentioned at least one reinforcing shoulder is located alongside said at least one lateral aperture or in a proximal position or in a distal position regarding said at least one lateral aperture.

The above mentioned aperture(s) may have any size or shape. The aperture(s) may have the shape of a circular, polygonal, oval or irregular hole or the shape of a slit which extends axially along the tubular wall. Preferably the distance between the distal end of the tube and said at least one aperture is equal or greater than 10 mm. The position of the aperture(s) may be located preferably next the distal end or the proximal end of the tube, or in a median position. If there is several apertures on the tube, they are preferably distant from one another on the periphery of the tube. The aperture in the shape of a slit may extend or not up to the proximal end of the tube.

According to an advantageous embodiment of the invention, the transparent tubular cannula overlies also at least a portion of the base-body while being removably connected to this portion, for example by screw threads.

The vascular needle system according to the invention are to be used for radial artery puncture, puncture of deep vessel, insertion of cannula or intra-vascular delivery of fluid volume or medication.

Other details and features of the present invention will appear in the appended claims.

Non-limitative embodiments of the invention will now be disclosed in a more detailed manner with reference to the drawings.

BRIEF DESCRIPTION OF THE DRAWINGS

FIG. 1 is an axial section through a vascular needle system according to the invention and FIG. 1a is a detailed view of the section with the threads between the base-body of the needle and the cannula.

FIGS. 2 and 2a are at an enlarged scale cross-sections along the line III-III of FIG. 1, illustrating two different embodiments of the vascular needle system according to the invention.

DETAILED DESCRIPTION OF THE INVENTION

Figure 3A:
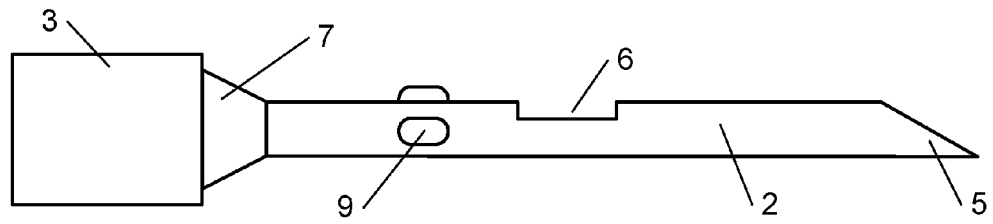
FIGS. 3a and 3b are lateral views of the vascular needle system where the needle is provided with reinforcing shoulders according to the invention.

On FIG. 1 a vascular needle system (plastic cannula (1) overlying a hollow metallic needle (2)) is illustrated. The plastic cannula (1) is made of a transparent material and is screwed over a plastic hub- or base-body (3) fastened to the proximal end (4) of the needle tube. The distal end (5) of the tube is beveled. The needle (2) may be a cylindric metallic tube which is slit in its body as illustrated on FIG. 1: the aperture (6) in the shape of a slit starts preferably at a distance of 1.5±0.5 cm from the beveled distal end (5) of the tube and extends toward the non-beveled proximal end (4). The aperture through the tubular wall of the needle may be of any size or shape, for example circular, polygonal, oval, irregular a.s.o.

The aperture (6) in the shape of a slit may end at the non-beveled proximal end or stops before reaching this end. The aperture (6) will allow a quick and direct assessment of the success of the puncture: in fact as soon as the beveled distal end (5) of the needle enters the vessel, the aperture (6) allows a direct visualization of the incoming blood; the blood flowing from the cavity of the needle through the tubular wall thereof will <<contaminate>> the space between the metallic needle (2) and the plastic cannula (1) giving a quick view of the puncture success.

For the puncture of small arteries, for example the radial artery, a 22 gauge metallic needle is preferably provided, the lumen of the plastic cannula overlying the needle allowing free passage for a 0.021" (0.53 mm) or thinner guide wire. The length of the cylindrical hollow needle is in this case preferably not longer than 3±1 cm from the beveled distal end (5) to the base-body (3): the reduced length suffices for puncture of the radial artery, which is quite superficial. The tip of the plastic cannula (1) is preferably tightly tapered and starts as close as possible from the beveled end of the metallic needle. The cannula is advantageously made of transparent or lightly tinted plastic material.

Moreover, the hub part (7) of the transparent cannula is made in such a way that the cannula is removably connected to the base-body (3) of the metallic needle. On FIG. 1, this connection is illustrated as threads (10) allowing a screwing of these two elements. This design is intended to secure together the cannula (1) and the metallic needle (2), allowing the operator to move freely back and forth the whole needle (2) when searching the vessel. The screw thread is preferably as minimal as required for securing the cannula (1) over the needle (2) and will preferably require a short unscrewing. Total length of the system is preferably only six (6) to seven (7) cm, with a base-body (3) of 3 cm to 3.5 cm, the needle (2) part itself, outside the base-body (3), being of 3±1 cm in length. The hub (7) of the cannula (1) is preferably luer-lock capable.

Other embodiments of the vascular needle system allow the use of larger sizes of needles for insertion of a large cannula as required for permanent infusion of large volume of fluid or for catheterization of deeper seated vessel (for example the femoral veins and arteries). These embodiments may be from gauge 21 to 16 (or less) and the total length of the needle can be as long as 9 cm or more.

The slit may start at a distance of 3 to 4 cm (or more) from the bevel of the needle, depending on the location and the depth of the vessel to be punctured with the system.

According to an embodiment illustrated on FIG. 2, the plastic cannula (1) has in cross-section a circular shape at the beveled part of the needle (2) and becomes oval at the level of the slit, thus increasing the space (8) between the plastic cannula (1) and the metallic needle (2) opposite to the aperture (6). According to another embodiment illustrated on FIG. 2a, the cavity is obtained via two reinforcing shoulders (9) located between said external surface of said tubular wall of said needle (2) and said internal surface of said cannula (1).

Longitudinal reinforcing shoulder(s) (9) (one or more, located along the slit (6)) start at the level of the slit and extend toward the base-body (3) of the needle (2).

Figure 3B:
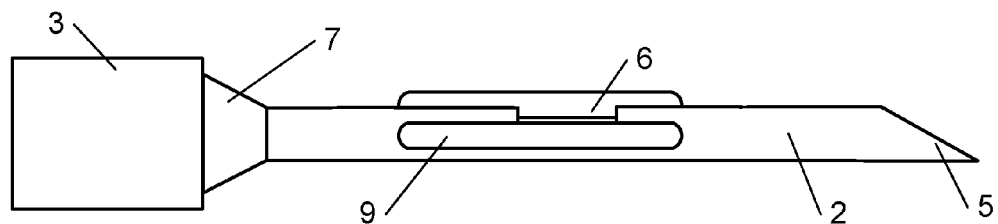

According to an embodiment illustrated on FIG. 3a, the external surface of the needle (2) is provided with two reinforcing shoulders (9) located in a proximal position regarding the aperture (6). On FIG. 3b, according to another embodiment, two reinforcing shoulders (9) are located alongside the aperture (6) on the external surface of the needle (2). These reinforcing shoulders (9), located on the external surface of the needle (2), maintain a distance between the internal surface of the cannula (1) and the external surface of the needle (2).

Figure 4A:
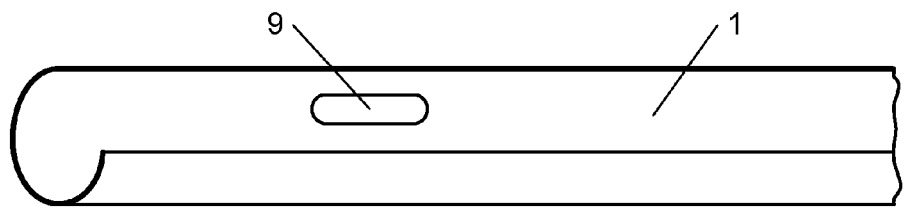
FIGS. 4a and 4b are broken perspective views of the cannula provided with reinforcing shoulders according to the invention.
Figure 4B:
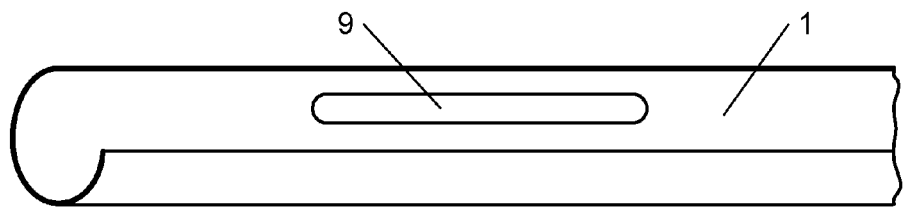

FIGS. 4a and 4b illustrate the internal surface of the cannula (1) provided with reinforcing shoulders (9) of different lengths. These reinforcing shoulders (9), located on the internal surface of the cannula (2), maintain a distance between the internal surface of the cannula (1) and the external surface of the needle (2).

Figure 5A:
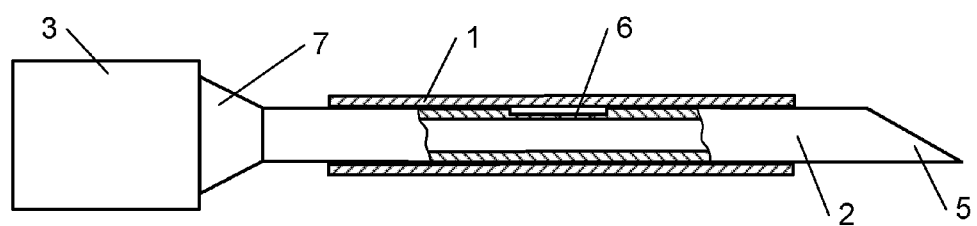
FIGS. 5a and 5b are respectively partial broken views of the vascular needle system where a part of the material forming the external wall of the needle is withdrawn and where a part of the material forming the internal wall of the cannula is withdrawn.
Figure 5B:
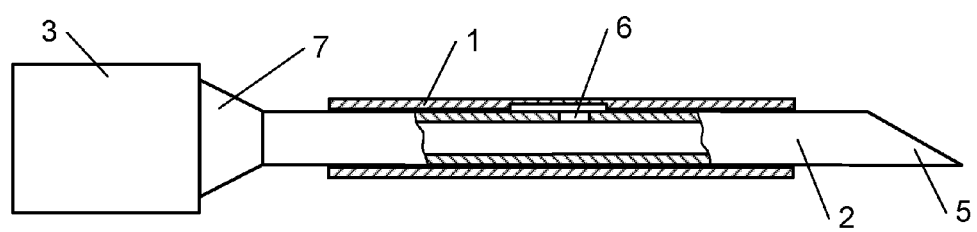

FIGS. 5a and 5b illustrate two different ways for the formation of the detection cavity. On FIG. 5a, a part of the material forming the external wall of the needle (2) is withdrawn while, on FIG. 5b, a part of the material forming the internal wall of the cannula (1) is withdrawn. In both cases, a detection cavity is formed between the aperture (6) and the internal surface of the cannula (1).

The invention claimed is:

1. A vascular needle system for visualization of blood, comprising a vascular needle comprising:
   a) a tube comprising a beveled distal end and a proximal end and between said ends a tubular wall comprising an external surface and an axial cavity for the passage of a fluid between said ends, said vascular needle comprising at least one lateral aperture and a proximal base-body fastened to the proximal end of the tube, and
   b) a transparent tubular cannula comprising an internal surface and at least partially overlying said needle, wherein said vascular needle system further comprises a detection cavity for said fluid, wherein said vascular needle system further comprises at least one reinforcing shoulder located between said external surface of said tubular wall of said needle and said internal surface of said cannula, said at least one lateral aperture maintained a distance from said cannula by said at least one reinforcing shoulder such that at least a portion of said external surface of said tubular wall of said needle directly contacts said internal surface of said cannula.

2. The vascular needle system of claim 1, wherein said at least one reinforcing shoulder is connected to said internal surface of said cannula.

3. The vascular needle system of claim 1, wherein said at least one reinforcing shoulder is connected to said external surface of said tubular wall of said needle.

4. The vascular needle system of claim 1, wherein said at least one reinforcing shoulder starts at the level of a slit of said needle and extends toward the base-body of the needle.

5. The vascular needle system of claim 1, wherein said at least one aperture has the shape of a circular, polygonal, oval or irregular hole or the shape of a slit which extends axially along the tubular wall.

6. The vascular needle system of claim 1, wherein the distance between the distal end of the tube and said at least one aperture is equal or greater than 10 mm.

7. The vascular needle system of claim 1, wherein said at least one aperture extends up to the proximal end of the tube.

8. The vascular needle system of claim 1, wherein said at least one aperture does not extend up to the proximal end of the tube.

9. The vascular needle system of claim 1, wherein at least two apertures are provided through said tubular wall, said at least two apertures being peripherally distant on said tube.

10. The vascular needle system of claim 1, wherein said transparent tubular cannula overlies at least a portion of a base-body of the vascular needle which is fastened to the proximal end of the tube, said cannula being removably connected to said portion of the base-body.

11. The vascular needle system of claim 10, wherein the cannula and said portion of the base-body are removably connected by screw threads.

12. The vascular needle system of claim 1, wherein said at least one reinforcing shoulder is a part of said internal surface of said cannula.

13. The vascular needle system of claim 1, wherein said at least one reinforcing shoulder is a part of said external surface of said tubular wall of said needle.

* * * * *